United States Patent
Ochi et al.

(10) Patent No.: US 10,775,331 B2
(45) Date of Patent: Sep. 15, 2020

(54) BIOLOGICAL INFORMATION MEASURING DEVICE, BIO SENSOR SYSTEM, AND ERROR DETECTION METHOD FOR BIOLOGICAL INFORMATION MEASURING DEVICE

(71) Applicant: PHC Holdings Corporation, Minato-ku, Tokyo (JP)

(72) Inventors: Mamiko Ochi, Ehime (JP); Takashi Miki, Ehime (JP); Daiki Mizuoka, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 580 days.

(21) Appl. No.: 15/603,392

(22) Filed: May 23, 2017

(65) Prior Publication Data
US 2017/0269013 A1 Sep. 21, 2017

Related U.S. Application Data

(62) Division of application No. 14/436,077, filed as application No. PCT/JP2013/007007 on Nov. 28, 2013, now abandoned.

(30) Foreign Application Priority Data

Nov. 28, 2012 (JP) .................. 2012-259349

(51) Int. Cl.
*G01N 27/327* (2006.01)
*G01N 33/49* (2006.01)
*G01N 27/00* (2006.01)

(52) U.S. Cl.
CPC ......... *G01N 27/00* (2013.01); *G01N 27/3273* (2013.01); *G01N 33/49* (2013.01)

(58) Field of Classification Search
CPC ....... G01N 27/327–3274; G01N 33/66; G01N 33/49; G01N 33/48785; G01N 33/487;
(Continued)

(56) References Cited

U.S. PATENT DOCUMENTS 5,502,396 A 3/1996 Desarzens et al.
8,603,768 B2 12/2013 Chatelier et al.
(Continued)

FOREIGN PATENT DOCUMENTS

JP 5-509163 12/1993
JP H07-167812 A 7/1995
(Continued)

OTHER PUBLICATIONS

Search Report from the corresponding International Patent Application No. PCT/JP2013/007007 dated Feb. 18, 2014.
(Continued)

*Primary Examiner* — Maris R Kessel
(74) *Attorney, Agent, or Firm* — Wenderoth, Lind & Ponack, L.L.P.

(57) ABSTRACT

In a biological information measurement device, the ingress of biological sample is detected even when a sensor is mounted, which reduces measurement error. The biological information measurement device comprises a voltage supply component that supplies voltage between first and second connectors, between second and third connectors, and between first and third connectors, a current measurement component that measures a first current that flows between the first and second connectors, a second current that flows between the second and third connectors, and a third current that flows between the first and third connectors, and a controller that is connected to the current measurement component and the voltage supply component. The controller compares two or more of the currents and thereby
(Continued)

determines whether a foreign substance has adhered between two or more connectors out of the first, second, and third connectors.

5 Claims, 14 Drawing Sheets

(58) Field of Classification Search
CPC .......... C12Q 1/00; C12Q 1/001; C12Q 1/004; C12Q 1/005; C12Q 1/006; C12Q 1/26–32; C12Q 1/34; C12Q 1/54; A61B 5/14532; A61B 5/14535; A61B 5/14536
See application file for complete search history.

(56) References Cited

U.S. PATENT DOCUMENTS

| | | | |
|---|---|---|---|
| 8,709,739 B2 | 4/2014 | Chatelier et al. | |
| 8,916,040 B2 | 12/2014 | Chatelier et al. | |
| 2003/0159945 A1* | 8/2003 | Miyazaki | G01N 33/48771 205/777.5 |
| 2006/0231423 A1 | 10/2006 | Harding et al. | |
| 2007/0131565 A1* | 6/2007 | Fujiwara | C12Q 1/001 205/777.5 |
| 2009/0184004 A1 | 7/2009 | Chatelier et al. | |
| 2010/0169035 A1 | 7/2010 | Liang et al. | |
| 2013/0068633 A1 | 3/2013 | Chatelier et al. | |
| 2013/0098763 A1 | 4/2013 | Chatelier et al. | |
| 2013/0204108 A1* | 8/2013 | Yoshioka | G01N 27/3274 600/347 |
| 2013/0337571 A1 | 12/2013 | Mizuoka et al. | |

FOREIGN PATENT DOCUMENTS

| | | | |
|---|---|---|---|
| JP | 11-108879 | 4/1999 | |
| JP | 2001-208715 A | 8/2001 | |
| JP | 2009-167812 A | 7/2009 | |
| JP | 2009-168815 A | 7/2009 | |
| JP | 2012-098031 A | 5/2012 | |
| WO | 92/01947 | 2/1992 | |
| WO | WO-2012056706 A1 * | 5/2012 | ......... A61B 5/14532 |
| WO | WO2012/153535 A1 | 11/2012 | |

OTHER PUBLICATIONS

Office Action from the co-pending U.S. Appl. No. 14/436,077 dated Dec. 5, 2016.
Office Action from the co-pending U.S. Appl. No. 14/436,077 dated Feb. 27, 2017.
Notice of Allowance from the corresponding Japanese Patent Application No. 2014-549834 dated Aug. 29, 2017.

* cited by examiner

| $X1 \leqq |Va-Vb| \leqq X2$ | 0 | 0 | 0 | 0 | 1 | 1 | 1 | 1 |
|---|---|---|---|---|---|---|---|---|
| $Y1 \leqq |Vb-Vc| \leqq Y2$ | 0 | 0 | 1 | 1 | 0 | 0 | 1 | 1 |
| $Z1 \leqq |Va-Vc| \leqq Z2$ | 0 | 1 | 0 | 1 | 0 | 1 | 0 | 1 |
| Determination results | Pass | error | error | error | error | error | error | error |

FIG. 9

| $V_{max} \leq L1$ | 0 | 0 | 1 | 1 |
|---|---|---|---|---|
| $V_{max} - V_{min} \geq U$ | 0 | 1 | 0 | 1 |
| Determination results | Pass | Pass | Pass | error |

FIG. 12

| | | | | |
|---|---|---|---|---|
| $L5 \leq Vmax \leq L6$ | 0 | 0 | 1 | 1 |
| $Vmax - Vmin \geq V$ | 0 | 1 | 0 | 1 |
| Determination results | Pass | Pass | Pass | error |

FIG. 14

BIOLOGICAL INFORMATION MEASURING DEVICE, BIO SENSOR SYSTEM, AND ERROR DETECTION METHOD FOR BIOLOGICAL INFORMATION MEASURING DEVICE

PRIORITY

This application is a divisional application of and claims priority to U.S. application Ser. No. 14/436,077 filed on Apr. 15, 2015, which is a National Stage Application under 35 U.S.C. § 365 of International Application PCT/JP2013/007007, with an international filing date of Nov. 28, 2013, which claims priority to Japanese Patent Application No. 2012-259349 filed on Nov. 28, 2012. The entire disclosures of U.S. application Ser. No. 14/436,077, International Application PCT/JP2013/007007 and Japanese Patent Application No. 2012-259349 are hereby incorporated herein by reference.

TECHNICAL FIELD

The disclosure relates to a biological information measurement device for measuring blood glucose levels or other such biological information from blood or another such biological sample.

BACKGROUND ART

A known biological information measurement device of this type comprises a main case, a sensor mounting component that is provided at the main case, first and second connectors that are provided at the sensor mounting component, a measurement voltage supply means for supplying voltage between the first and second connectors, a current measurement means for measuring a first current that flows between the first and second connectors, and a controller that is connected to the measurement voltage supply means and the current measurement means. The controller is also connected to a mounting detection means for detecting the mounting of a sensor to the sensor mounting component (see Patent Literature 1, for example).

With a biological information measurement device such as this, biological information can be measured by mounting a biosensor to the sensor mounting component, supplying voltage from the measurement voltage supply means between the first and second connectors, and measuring the current that flows between the first and second connectors with the current measurement means. Even in a state in which no mounting of a sensor to the sensor mounting component has been detected and a biological sample has accidentally flowed in between the first and second connectors, the current flowing between the first and second connectors can still be measured by the current measurement means. In this case, however, the fact that no biosensor has been mounted to the sensor mounting component is detected ahead of time by the detection means. Thus, the ingress of the biological sample between the first and second connectors at the sensor mounting component can be detected at this point.

CITATION LIST

Patent Literature

Patent Literature 1: Japanese Laid-Open Patent Application 2012-098031

SUMMARY

Technical Problem

As discussed above, in the above prior art, when no biosensor is mounted, it is possible to detect that a biological sample has accidentally flowed in between the first and second connectors. In a state in which a biosensor is mounted to the sensor mounting component, however, it cannot be detected that a biological sample has accidentally flowed in between the first and second connectors, and as a result, a significant error ends up occurring in the measurement results for the biological information.

Specifically, in a state in which a biosensor has been mounted to the sensor mounting component, this mounting is detected by the mounting detection means, and the controller measures the biological information from the current flowing between the first and second connectors measured by the current measurement means. However, the current flowing between the first and second connectors may reflect not only the biosensor portion, but also the biological sample that has accidentally flowed in between the first and second connectors, in which case there will be a significant error in the measurement results.

In view of this, it is an object of this disclosure to reduce measurement error by detecting the adhesion of a foreign substance between connectors even when a bio sensor is mounted.

Solution to Problem

In one aspect of this disclosure, a biological information measurement device comprises a main case, a sensor mounting component, first, second, and third connectors that are provided at the sensor mounting component, a voltage supply component, a current measurement component, and a controller. The sensor mounting component is provided at the main case and mounts a sensor for measuring biological information on the basis of a biological sample. The voltage supply component supplies voltage between the first connector and the second connector, between the second connector and the third connector, and between the first connector and the third connector. The current measurement component measures a first current that flows between the first connector and the second connector, a second current that flows between the second connector and the third connector, and a third current that flows between the first connector and the third connector. The controller controls the current measurement component and the voltage supply component. The controller compares two or more of the first current, the second current, and the third current measured by the current measurement component in a state in which a sensor has been mounted to the sensor mounting component, and thereby determines whether a foreign substance has adhered between two or more of the first connector, the second connector, and the third connector.

Another aspect of this disclosure is a method for error detection in a biological information measurement device comprising a sensor mounting component configured to mount a sensor to measure biological information on the basis of a biological sample, and first, second, and third connectors that are provided at the sensor mounting component. The error detection method comprises applying voltage between the first and second connectors, the second and third connectors, and the first and third connectors, measuring a first current that flows between the first and second connectors, a second current that flows between the second and third connectors, and a third current that flows between the first and third connectors, comparing two or more of the first current, the second current, and the third current in a state in which a sensor has been mounted to the sensor mounting component, and determining whether a foreign substance has adhered between two or more of the first, second, and third connectors on the basis of the comparison result.

Advantageous Effects

The biological information measurement device is effective at reducing measurement error by detecting the adhesion of foreign substances between connectors, even when a biosensor is mounted.

BRIEF DESCRIPTION OF DRAWINGS

FIG. 9 is a determination table produced by the liquid ingress determination processing;

FIG. 12 is a determination table produced by the liquid ingress determination processing;

FIG. 14 is a determination table produced by this error determination processing.

DETAILED DESCRIPTION

Embodiments will now be described through reference to the drawings as needed. However, some unnecessary detailed description may be omitted. For example, description of already known facts or redundant description of components that are substantially the same may be omitted. This is to avoid unnecessary repetition in the following detailed description, and facilitate an understanding on the part of a person skilled in the art. The inventors have provided the appended drawings and the following description so that a person skilled in the art might fully understand this disclosure, but do not intend for these to limit what is discussed in the patent claims.

Certain embodiments of the present invention will now be described through reference to the appended drawings.

Embodiment 1

1-1 Configuration
1-1-1 Blood Glucose Level Measurement Device 100

Figure 1:
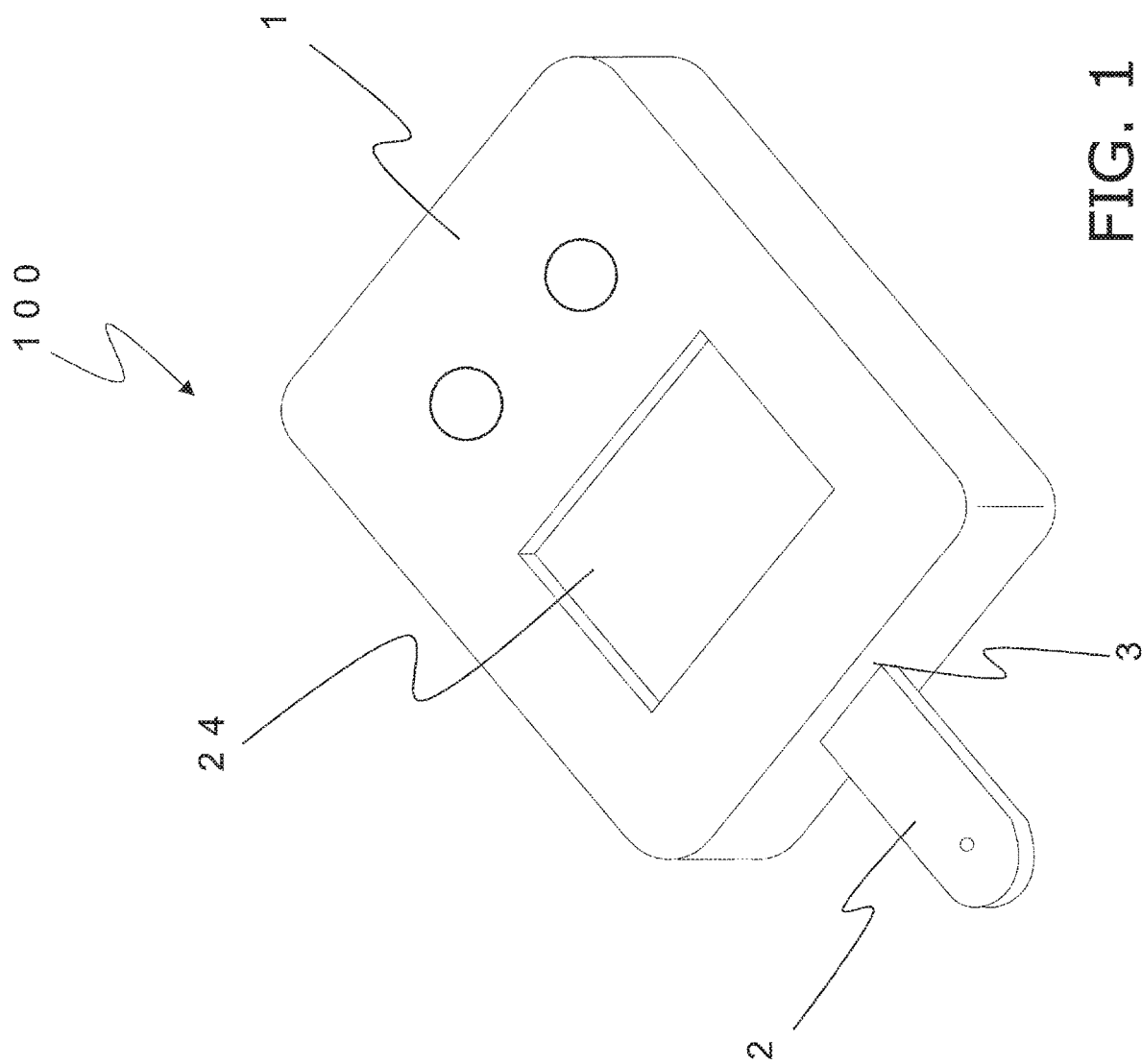
FIG. 1 is an oblique view of the biological information measurement device pertaining to Embodiment 1.

FIG. 1 is an oblique view schematically showing the appearance of the blood glucose level measurement device 100 pertaining to this embodiment (an example of a biological information measurement device). The blood glucose level measurement device 100 has a main case 1, an insertion opening 3 (an example of a sensor mounting component) for a biosensor 2 at one end of the main case 1, and a display component 24, such as a liquid crystal display (LCD) or an organic electroluminescent display (OLED), at the front of the main case 1.

1-1-2 Configuration of Biosensor

Figure 2:
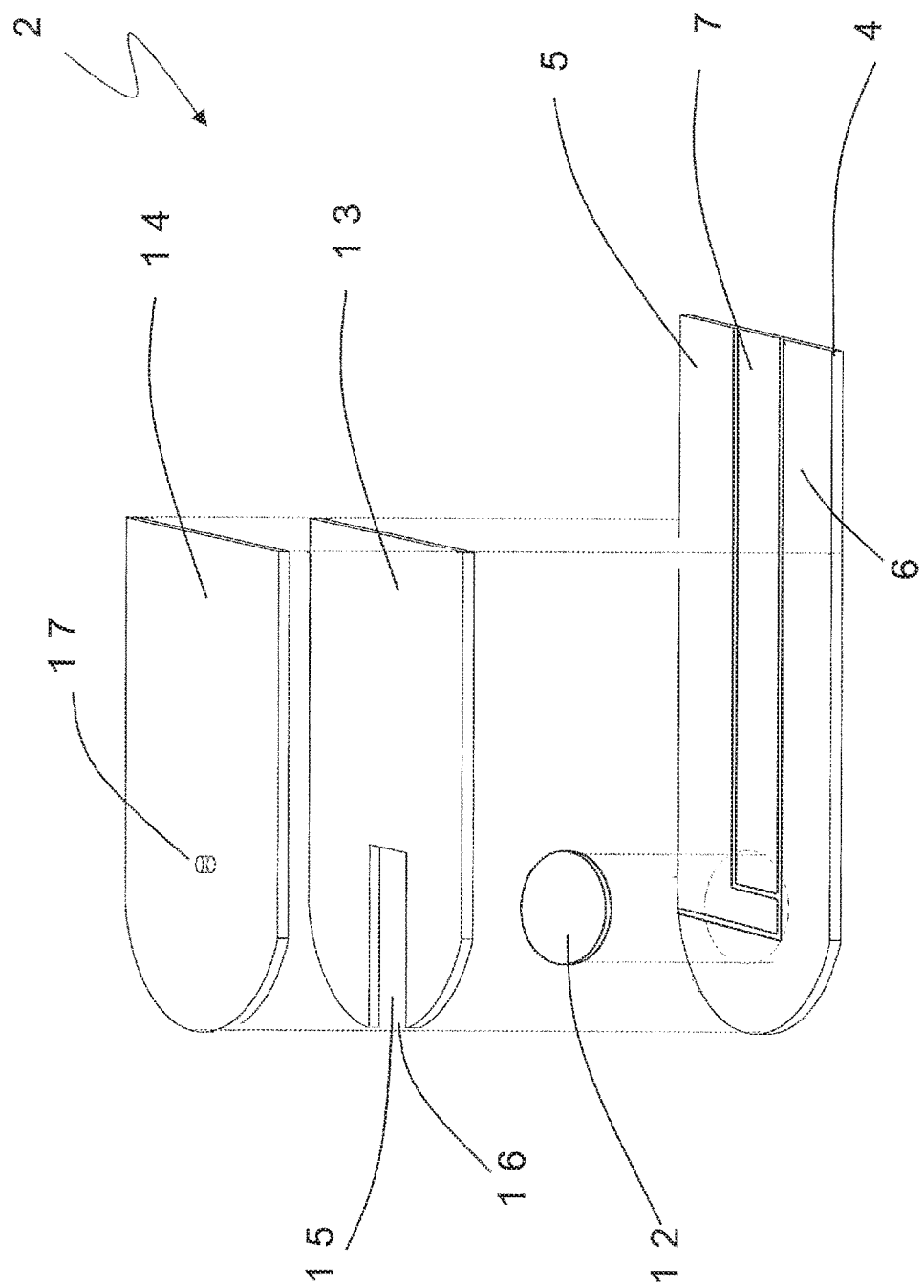
FIG. 2 is an exploded view of a biosensor to be mounted to the biological information measurement device.

As shown in FIG. 2, the biosensor 2 has three electrodes disposed opposite each other and at a specific spacing at one end (the right side in FIG. 2) of a rectangular insulated substrate 4. These electrodes consist of a blood component measurement working electrode 5, a blood component measurement counter electrode 6, and a blood component detecting electrode 7.

Figure 4:
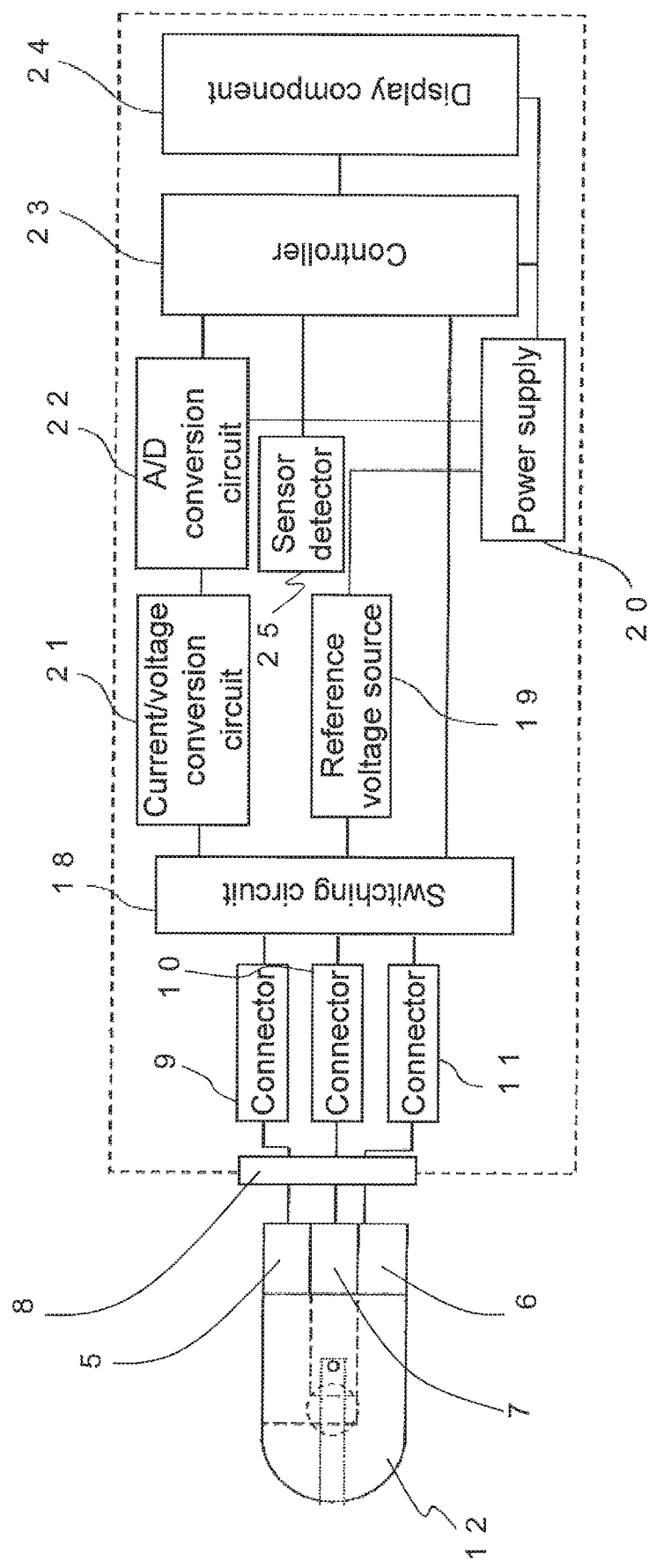
FIG. 4 is a control block diagram of the biological information measurement device.

The blood component measurement working electrode 5, the blood component measurement counter electrode 6, and the blood component detecting electrode 7 are inserted into the main case 1 through the insertion opening 3 of the blood glucose level measurement device 100 shown in FIG. 1, and are electrically connected by coming into contact with connectors 9, 10, and 11 of an input terminal 8 (FIG. 4; discussed below). More specifically, the blood component measurement working electrode 5 of the biosensor 2 is connected to the connector 9, the blood component measurement counter electrode 6 is connected to the connector 11, and the blood component detecting electrode 7 is connected to the connector 10.

Figure 3:
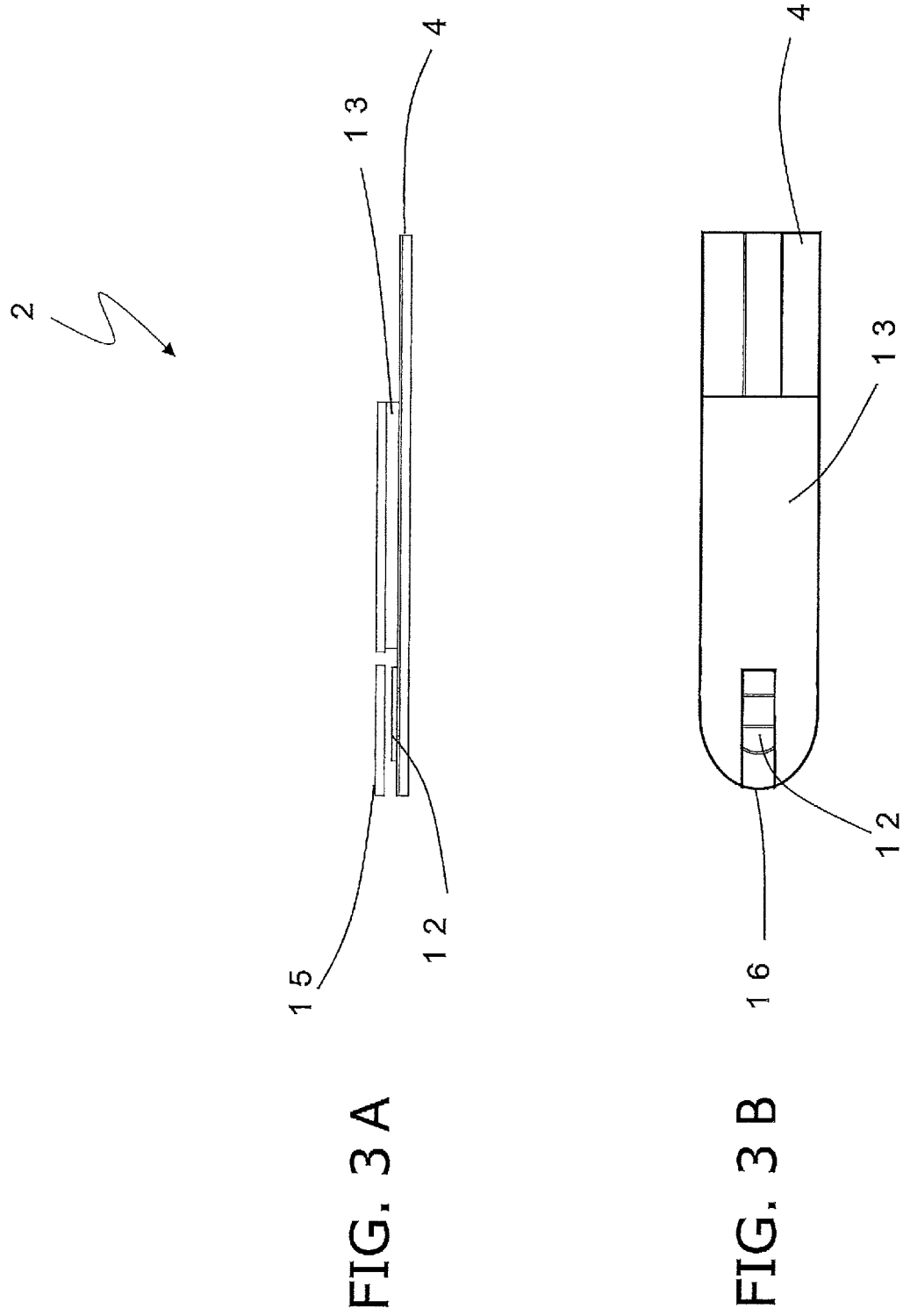
FIGS. 3A and 3B are a side view and a plan view of the biosensor.

As shown in FIGS. 2 and 3A, at the other end of the biosensor 2 (the left side in FIG. 2; the opposite side from the insertion side into the insertion opening 3), a reagent 12 is disposed extending over the blood component measurement working electrode 5, the blood component measurement counter electrode 6, and the blood component detecting electrode 7. In this state, the blood component measurement working electrode 5, the blood component measurement counter electrode 6, and the blood component detecting electrode 7 are connected via the reagent 12.

The reagent 12 includes glucose dehydrogenase or another such redox enzyme, and a mediator, and may also include a buffer, a polymer material, an enzyme stabilizer, a crystal homogenizer, or other such additives as desired.

As shown in FIG. 2, a cover 14 is disposed over the insulated substrate 4 and the reagent 12 with a spacer 13 in between. Meanwhile, at one end of the insulated substrate 4 (the right side in FIG. 2), as shown in FIGS. 2 and 3A, the blood component measurement working electrode 5, the blood component measurement counter electrode 6, and the blood component detecting electrode 7 are not covered by the spacer 13 or the cover 14, and are exposed. As mentioned above, the exposed blood component measurement working electrode 5, the blood component measurement counter electrode 6, and the blood component detecting electrode 7 are electrically connected to the connectors 9 to 11 at the input terminal 8.

As shown in FIG. 2, a biological sample introduction path 15 for introducing blood is formed in the spacer 13 of the biosensor 2. This biological sample introduction path 15 extends from the other end of the biosensor 2 (the left side in FIG. 2) to above the reagent 12, and the other end that opens to the outside serves as a biological sample supply port 16.

As can be seen from FIG. 2, the blood component measurement counter electrode 6 is the one disposed closest to the biological sample supply port 16, after which comes the blood component measurement working electrode 5, and finally the blood component detecting electrode 7. That is, the blood component measurement working electrode 5, the blood component measurement counter electrode 6, and the blood component detecting electrode 7 are disposed in that order starting from the biological sample supply port 16.

An air hole 17 is formed in the cover 14 of the biosensor 2. The air hole 17 is used to promote capillary action when blood is deposited in the biological sample supply port 16, and to allow this blood to flow to a portion of the blood component measurement counter electrode 6 that is past the blood component measurement working electrode 5, or up to the blood component detecting electrode 7. Thus, the air hole 17 is provided at a place that is opposite a portion of the blood component detecting electrode 7.

Next, the constituent elements of the biosensor 2 will be described in further detail.

There are no particular restrictions on the material of the insulated substrate 4, but examples of materials that can be used include polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylic resin (PMMA), ABS resin (ABS), and glass. Of these, polyethylene terephthalate (PET), polycarbonate (PC), and polyimide (PI) are preferable, and polyethylene terephthalate (PET) is more preferable.

There are no particular restrictions on the size of the insulating substrate, but an example is an overall length of 5 to 100 mm, a width of 2 to 50 mm, and a thickness of 0.05 to 2 mm; preferably an overall length of 7 to 50 mm, a width of 3 to 20 mm, and a thickness of 0.1 mm to 1 mm; and more preferably an overall length of 10 to 40 mm, a width of 3 to 10 mm, and a thickness of 0.1 to 0.6 mm.

The electrodes on the insulated substrate 4 can be formed, for example, by forming a conductive layer of gold, platinum, palladium, or another such material by sputtering or vapor deposition, and then working the conductive layer into a particular electrode pattern with a laser to form the blood component measurement counter electrode 6, the blood component measurement working electrode 5, and the blood component detecting electrode 7. Examples of the laser include a YAG laser, a $CO_2$ laser, and an excimer laser.

Covering the surface of the blood component measurement counter electrode 6, the blood component measurement working electrode 5, and the blood component detecting electrode 7 can be accomplished, for example, by preparing a solution of a polymer material, dropping or applying this solution onto the electrode surface, and then drying. The drying can be, for example, natural drying, air drying, hot forced air drying, heated drying, or the like.

As discussed above, the reagent 12 includes glucose dehydrogenase or another such redox enzyme, a mediator, and an adhesive, and may optionally contain a buffer, a polymer material, an enzyme stabilizer, a crystal homogenizer, or other such constituents as desired. When the reagent 12 is prepared with water, the water makes up the bulk of it, followed by the redox enzyme, then the mediator, and then other substances including additives such as buffers. Also, since the water has evaporated from the reagent 12 after drying, the redox enzyme ends up being the bulk of it, then, the mediator, and then the additive and other substances.

There are no particular restrictions on the mediator used in the biosensor, but examples include ferricyanides, p-benzoquinone, p-benzoquinone derivatives, phenazine methosulfate, methylene blue, ferrocene, phenothiazine and its derivatives. Also, "quinone compound" refers to a compound that contains quinone. Quinone compounds include quinone and quinone derivatives. Examples of quinone derivatives include compounds in which various functional groups (also referred to as substituents) have been added to a quinone. Examples of the quinone in the quinone compound include benzoquinone, naphthoquinone, anthraquinone, phenanthrenequinone, and phenanthroline quinone. A specific example of phenanthrenequinone is 9,10-phenanthrenequinone. There are no particular restrictions on the amount in which the mediator is contained, but an example is 0.1 to 1000 mM per measurement or per biosensor, preferably 1 to 500 mM, and more preferably 10 to 200 mM.

Examples of the redox enzyme include glucose oxidase, lactate oxidase, cholesterol oxidase, bilirubin oxidase, glucose dehydrogenase, and lactate dehydrogenase. An example of the amount of redox enzyme is 0.01 to 100 U per measurement or per sensor, preferably 0.05 to 10 U, more preferably 0.1 to 5 U. Of these, using glucose as what is measured is preferred, in which case the redox enzyme is preferably glucose dehydrogenase or glucose oxidase.

As discussed above, the reagent 12 includes glucose dehydrogenase or another such redox enzyme, a mediator, and an adhesive, and may optionally include a buffer, a polymer material, an enzyme stabilizer, a crystal homogenizer, or the like as needed, but to prepare this reagent, these various substances are dissolved in water that is approximately 80% of the total amount, and this solution is dropped onto the blood component measurement counter electrode 6, the blood component measurement working electrode 5, and the blood component detecting electrode 7 and then dried. At the time of preparation, water is the most prevalent component, then the enzyme (redox enzyme, etc.), then the mediator, and then the additives and other substances, but in a dried state the water is completely evaporated, so the enzyme (redox enzyme, etc.) becomes most prevalent, then the mediator, and then the additives and other substances.

There are no particular restrictions on the material of the spacer 13, but it can be the same as the material of the insulated substrate 4, for example. There are no particular restrictions on the size of the spacer 13, either, but an example is an overall length of 5 to 100 mm, a width of 2 to 50 mm, and a thickness of 0.01 to 1 mm; preferably an overall length of 7 to 50 mm, a width of 3 to 20 mm, and a thickness of 0.05 mm to 0.5 mm; and more preferably an overall length of 10 to 30 mm, a width of 3 to 10 mm, and a thickness of 0.05 to 0.25 mm. Further, an I-shaped cut-out that serves as the biological sample introduction path 15 for introducing blood is formed in the spacer 13.

There are no particular restrictions on the material of the cover 14, but it can be the same as the material of the insulated substrate 4, for example. It is preferable if the portion of the cover 14 corresponding to the ceiling of the biological sample introduction path 15 is subjected to a hydrophilic treatment. Examples of a hydrophilic treatment include a method in which a surfactant is applied, and a method in which hydrophilic functional groups such as hydroxyl groups, carbonyl groups, or carboxyl groups are introduced onto the surface (rear face) of the cover 14 by plasma treatment or the like. There are no particular restrictions on the size of the cover 14, but an example is an overall length of 5 to 100 mm, a width of 3 to 50 mm, and a thickness of 0.01 to 0.5 mm; preferably an overall length of 10 to 50 mm, a width of 3 to 20 mm, and a thickness of 0.05 mm to 0.25 mm; and more preferably an overall length of 15 to 30 mm, a width of 5 to 10 mm, and a thickness of 0.05 to 0.1 mm. The air hole 17 is preferably formed in the cover 14, and examples of its shape include circular, elliptical, and polyhedral. An example of its size is a maximum diameter of 0.01 to 10 mm, preferably a maximum diameter of 0.05 to 5 mm, and more preferably a maximum diameter of 0.1 to 2 mm. The air hole 17 may be formed, for example, by making a hole with a drill or a laser, or it may be formed when the cover 14 is formed, using a mold that can form an air vent.

As shown in FIG. 2, the biosensor 2 can be manufactured by laminating the insulated substrate 4, the spacer 13, and the cover 14 in that order, and then integrating them. This integration can be accomplished by affixing the insulated substrate 4, the spacer 13, and the cover 14 with an adhesive, or by thermally fusing them together. Examples of adhesives that can be used include epoxy adhesives, acrylic adhesives, polyurethane adhesives, thermosetting adhesives (such as hot melt adhesives), and UV-setting adhesives.

The cover 14 is transparent or semi-transparent so that the flow of blood into the biological sample introduction path 15 can be monitored visually.

1-1-3 Configuration of Blood Glucose Level Measurement Device 100

The configuration inside the main case 1 of the blood glucose level measurement device 100 will now be described through reference to FIG. 4. The blood glucose level measurement device 100 comprises the connectors 9 to 11, a switching circuit 18 connected to the connectors 9 to 11, a reference voltage source 19 (an example of a voltage supply component), a power supply 20, a current/voltage conversion circuit 21, an A/D conversion circuit 22, a controller 23 (an example of a controller), the display component 24, and a sensor detector 25 (an example of a sensor detector).

The reference voltage source 19 is connected via the switching circuit 18 to the connectors 9 to 11. The reference voltage source 19 is also connected to the power supply 20, which supplies power to the various components. The switching circuit 18 is connected to the controller 23 via the current/voltage conversion circuit 21 and the A/D conversion circuit 22.

The controller 23 includes a CPU or other such processor, and executes processing (discussed below) by executing a specific program read from a memory.

The current/voltage conversion circuit 21 detects the current that flows to the connectors 9 to 11 and converts this current into voltage. This voltage is converted by the A/D conversion circuit 22 into a digital signal. The controller 23 senses the voltage value (converted from a current value) on the basis of this digital signal. The controller 23 determines a blood glucose level or other such information from this voltage value. Therefore, in this embodiment, the current/voltage conversion circuit 21 and the A/D conversion circuit 22 constitute a current measurement means.

The controller 23 is connected to the display component 24, which allows blood glucose levels and other such biological information, or other information (including malfunction information), to be displayed on the display component 24. Furthermore, the controller 23 is connected to the sensor detector 25, which detects the mounting of the biosensor 2 to the insertion opening 3. This sensor detector 25 may be the detection means used in the above-mentioned Patent Literature 1, for example.

1-2 Operation
1-2-1 Blood Glucose Level Measurement

FIG. 5 shows the amount of current and the applied voltage during measurement of a blood glucose level with the blood glucose level measurement device 100 and this type of biosensor 2.

As shown in FIG. 1, when the biosensor 2 is inserted into the insertion opening 3, the sensor detector 25 detects this insertion. When the controller 23 detects the insertion of the biosensor 2, it applies voltage between the connectors 9 to 11 from the reference voltage source 19 and via the switching circuit 18. This voltage is the applied voltage VA supplied during the first application period T1 in FIG. 5a. The connectors 9 to 11 are connected to the blood component measurement working electrode 5 and the blood component measurement counter electrode 6 of the biosensor 2.

After this, an applied voltage VB is supplied from the reference voltage source 19 via the switching circuit 18 during a second application period T2. The blood glucose level is measured by the controller 23 at the 15 second point in FIG. 5a, and this measurement value is displayed on the display component 24.

Figure 5A:
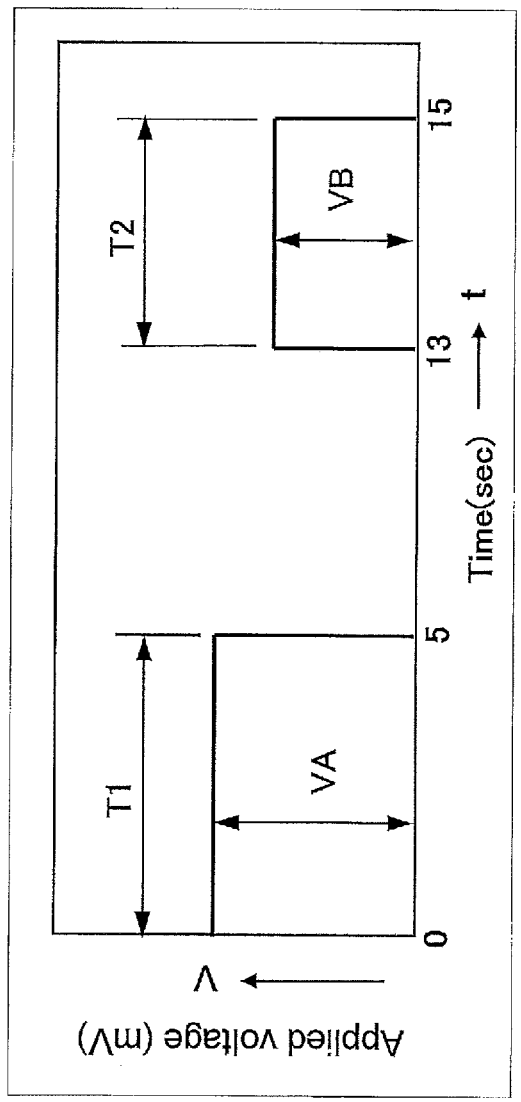
FIGS. 5A and 5B are graphs of the applied voltage and the current value in the biological information measurement device.
Figure 5B:
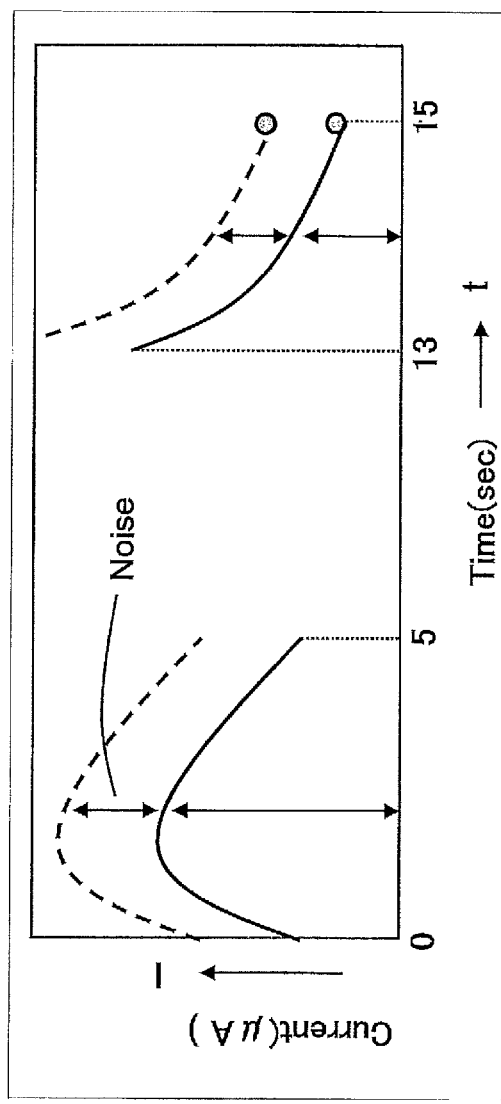

FIG. 5b shows the current that flows between the blood component measurement working electrode 5 and the blood component measurement counter electrode 6 of the biosensor 2 during the above-mentioned voltage application in FIG. 5a. In FIG. 5b, the solid lines are the normal amount of current, and the broken lines are the amount of current when blood or another such foreign substance has accidentally adhered to the blood component measurement working electrode 5 and the blood component measurement counter electrode 6, for example.

For instance, when the measurement is executed in the state in FIG. 1, if a large amount of blood should be deposited on the surface of the biosensor 2, the blood will spread over the surface of the bio sensor 2 and flow through the insertion opening 3 into the main case 1, where it will reach the connectors 9 to 11. If the current that flows between the blood component measurement working electrode 5 and the blood component measurement counter electrode 6 of the biosensor 2 is measured in this state, the current that flows between the connectors 9 to 11 will be added in, and as a result the amount of current detected by the controller 23 will end up being larger than the amount in the normal state, and this will be a measurement error, as shown by the broken lines in FIG. 5b. That is, the broken lines in FIG. 5b show the waveform of this added noise component.

In view of this, in this embodiment, the current is measured between the connectors 9 and 11, between the connectors 9 and 10, and between the connectors 10 and 11 prior to the first application period T1 in FIG. 5a (that is, before the voltage for measurement is applied), and as a result, the above-mentioned unintended ingress of blood (an example of the adhesion of a foreign substance) to the connectors 9 to 11 is detected.

Also, in this embodiment, as mentioned above, the amount of current is converted by the current/voltage conversion circuit 21 and the A/D conversion circuit 22 into voltage, which is detected by the controller 23.

1-2-2 Overall Operation of Blood Glucose Level Measurement Device 100

Figure 6:
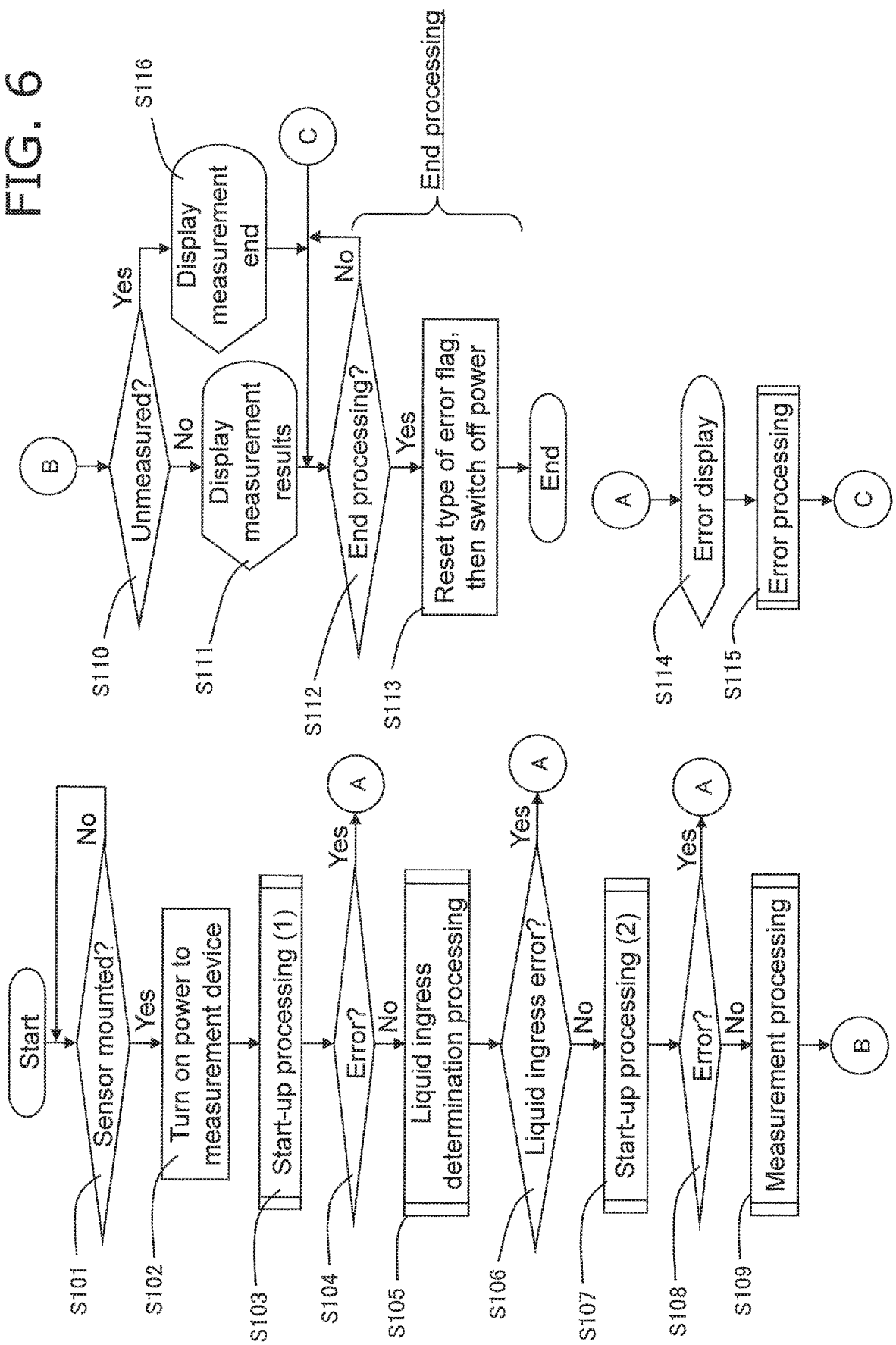
FIG. 6 is a flowchart of the overall operation of the biological information measurement device.

FIG. 6 is a flowchart of the overall operation of the blood glucose level measurement device 100 pertaining to this embodiment.

First, in this embodiment, as shown in FIG. 1, when the biosensor 2 is inserted into the insertion opening 3, this insertion is detected by the sensor detector 25 (step S101).

When the insertion of the biosensor 2 is detected, the controller 23 actuates the main power supply of the blood glucose level measurement device 100 (step S102).

After this, the controller 23 performs a predetermined start-up processing 1 (step S103). The predetermined start-up processing 1 here runs a self-check on the blood glucose level measurement device 100, confirms the temperature, identifies the front and back of the sensor, and so forth.

After the specific start-up processing 1, the controller 23 performs error determination (step S104). When an error is detected in any check, the error is outputted and displayed on the display component 24 (step S114), and predetermined error processing is performed (step S115).

This predetermined error processing involves storing error history in a memory, increasing the error count by type of error (that is by error code) and recording this to the memory, or the like.

After this, the controller 23 resets an error flag or the like and then shuts off the main power (step S113) as described below when any of the following conditions is met (step S112), namely, when the sensor detector 25 has detected that the biosensor 2 has been removed from the insertion opening 3, or when shut-off of the main power supply by the user has been detected, or when a specific length of time (such as three minutes) has elapsed since the end of the previous processing (this is usually called end processing; the same applies hereinafter).

On the other hand, if no error has been detected in the specific start-up processing 1, the controller 23 performs liquid ingress determination processing (discussed below) (steps S105 and S106).

If the controller 23 detects liquid ingress in the liquid ingress determination processing, the error (in this case, a "liquid ingress" error) is outputted, the error details are displayed (in this case, a display indicating that there is a "liquid ingress" error) (step S114), and the predetermined error processing is performed (step S115).

On the other hand, if no liquid ingress is detected in the liquid ingress determination processing, predetermined start-up processing 2 is performed (step S107). In the start-up processing 2, for example, a non-compatible sensor is identified, or a used sensor is identified.

After the start-up processing 2, the controller 23 performs error determination (step S108). If an error is detected in any determination, the controller 23 outputs the error and displays it on the display component 24 (step S114). For instance, if the biosensor 2 is not compatible with the value measurement device 100, the controller 23 outputs an "incompatible" error and displays it on the display component 24, and after the predetermined error processing (step S115), the end processing is performed (steps S112 and S113). Also, if the biosensor 2 is a used sensor, the controller 23 outputs a "used" error and displays it on the display component 24, and after the predetermined error processing (step S115), the end processing is performed (steps S112 and S113).

When an error is not detected in the start-up processing 2, the controller 23 performs processing to measure a blood glucose level (discussed below) (step S109).

After the measurement processing, the controller 23 determines whether or not a blood glucose level has been measured (step S110). If a blood glucose level has been measured, the measured result is displayed on the display component 24 (step S111), after which the above-mentioned end processing is performed (steps S112 and S113). That is, the controller 23 determines whether or not the sensor detector 25 has detected that the biosensor 2 has been removed from the insertion opening 3, or it has been detected that the user has switched off the main power supply, or it has been determined that a specific amount of time (such as three minutes) has elapsed since the end of the previous processing (step S112), and if any of these conditions is met, an error flag or the like is reset as discussed below, and the main power supply is shut off (step S113).

On the other hand, if no blood glucose level has been measured (such as when no blood is deposited even though the deposit standby time has elapsed), the controller 23 switches the display on the display component 24 from a display of the deposit standby state (discussed below) to a display indicating that the process ends without any measurement (step S116), and the end processing is performed (steps S112 and S113).

In this case, the power may be switched off right away, without doing any processing, after the deposit standby time has elapsed.

1-2-3 Error Determination Processing

Figure 7:
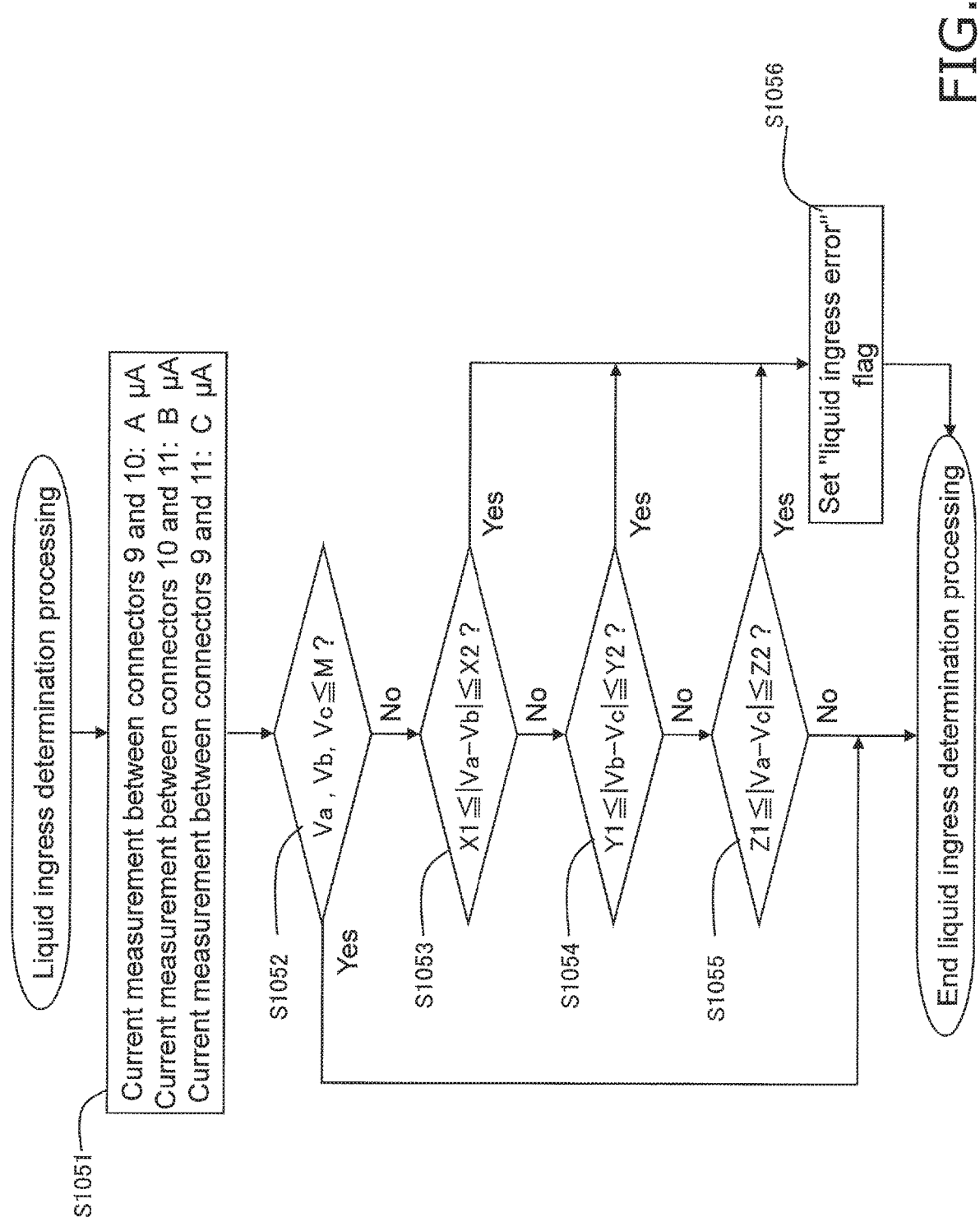
FIG. 7 is a flowchart of the liquid ingress determination processing performed by the biological information measurement device.

FIG. 7 shows the details of the processing in S105 in FIG. 6, and shows error determination processing due to liquid ingress, which is a feature of this embodiment (hereinafter also referred to as liquid ingress determination processing).

After the specific start-up processing 1 (if no error is identified), the controller 23 supplies a specific voltage from the reference voltage source 19, through the switching circuit 18, between the connectors 9 and 10, between the connectors 10 and 11, and between the connectors 9 and 11. The current that flows between the connectors 9 and 10, between the connectors 10 and 11, and between the connectors 9 and 11 is converted into voltage by the current/voltage conversion circuit 21, after which the voltage is converted into a numerical value by the A/D conversion circuit (analog/digital conversion circuit) 22. The controller 23 measures this digitized voltage value as a detected voltage value.

Figure 8:
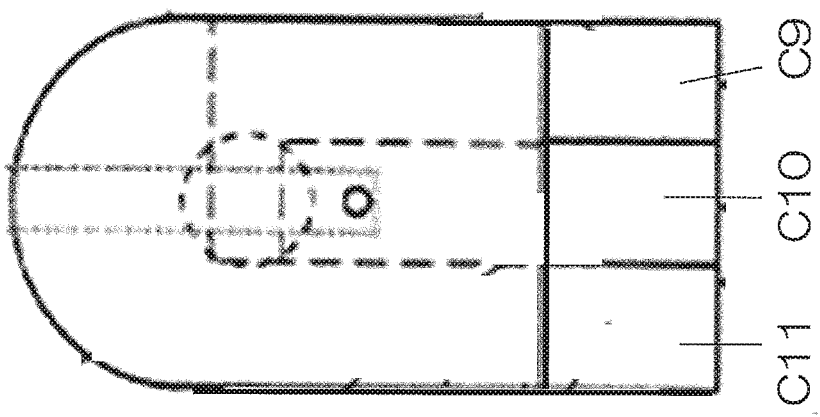
FIG. 8 is a diagram illustrating the current between connectors, for liquid ingress determination processing performed by the biological information measurement device.

More specifically, as shown in FIG. 8, the controller 23 acquires a current A ($\mu$A) between the connectors 9 and 10 (labeled as "between C9 and C10" in FIG. 8), a current B ($\mu$A) between the connectors 10 and 11 (labeled as "between C10 and C11" in FIG. 8), and a current C ($\mu$A) between the connectors 9 and 11 (labeled as "between C9 and C11" in FIG. 8) (step S1051).

The controller 23 then determines whether or not voltage values Va, Vb, and Vc, obtained by converting current A, current B, and current C with the current/voltage conversion circuit 21 and the A/D conversion circuit 22, are equal to or less than a specific threshold M (an example of a second threshold) (step S1052). M is a value corresponding to an amount of current used for confirming conductivity between terminals, and is set in a range of values corresponding to 0 to 3 $\mu$A. For example, if this is only used to confirm conductivity, it may be set to 0 $\mu$A (0 V), but if conductivity from something other than liquid ingress, such as absorption of reagent moisture, is excluded, it may be set to a value that exceeds 0 $\mu$A. If all of Va, Vb, and Vc do not exceed the specific threshold M, it is concluded that at least no liquid ingress has occurred, the liquid ingress determination processing is ended. The flow proceeds to the start-up processing 2 of step S107 in FIG. 6, and then moves on to the measurement processing (step S109 in the drawing).

If any of Va, Vb, and Vc exceeds the specific threshold M, the controller 23 determines whether or not the differences between Va, Vb, and Vc (here, |Va−Vb|, |Vb−Vc|, and |Va−Vc|, respectively) are within a specific range, and it is determined that there is liquid ingress if one of them is within this specific range. The thresholds X1, X2, Y1, Y2, Z1, and Z2 discussed below are determined by finding the optimal value from numerous measured values. X1, X2, Y1, Y2, Z1, and Z2 may be individually set by the system, or if there is no need for them to be set individually, they may be set to X1=Y1=Z1, and X2=Y2=Z2. The ranges, for example, are such that X1, Y1, and Z1 are values each corresponding to 0 to 3 µA, and X2, Y2, and Z2 are set to values each corresponding to 3 to 25 µA. However, these are set to satisfy the conditions of X1<X2, Y1<Y2, Z1<Z2.

More specifically, the controller 23 determines X1≤|Va−Vb|≤X2 (step S1053), and sets a "liquid ingress error" flag (step S1056) and ends the liquid ingress determination processing if |Va−Vb| is within the range of X1 to X2.

After this, the flow moves to the above-mentioned error display and error processing (steps S114 and S115 in FIG. 6).

The controller 23 proceeds to step S1054 if |Va−Vb| is outside the range of X1 to X2.

The controller 23 determines Y1≤|Vb−Vc|≤Y2 (step S1054), and sets a "liquid ingress error" flag (step S1056), ends the liquid ingress determination processing as discussed above, and moves on to error display and error processing if |Vb−Vc| is within the range of Y1 to Y2 (steps S114 and S115 in FIG. 6).

The controller 23 proceeds to step S1055 if |Vb−Vc| is outside the range of Y1 to Y2.

The controller 23 determines Z1≤|Va−Vc|≤Z2 (step S1055), and sets a "liquid ingress error" flag (step S1056), ends the liquid ingress determination processing as discussed above, and moves on to error display and error processing if |Va−Vc| is within the range of Z1 to Z2 (steps S114 and S115 in FIG. 6).

Meanwhile, if |Va−Vc| is outside the range of Z1 to Z2, and it is determined that there is no liquid ingress, the flow proceeds to the start-up processing 2 before the measurement processing in step S107 FIG. 6 (step S107).

FIG. 9 shows a determination table produced by this liquid ingress determination processing. As shown in the drawing, if |Va−Vb|, |Vb−Vc|, and |Va−Vc| are all outside the range of the specific threshold, it is determined that there is no ingress of blood or the like into the connector 9, 10, or 11 portion. On the other hand, if any of |Va−Vb|, |Vb−Vc|, and |Va−Vc| is within the range of the specific threshold, it is determined that there is a high probability that blood or the like has flowed into the connector 9, 10, or 11 portion. That is, in a state in which there is no ingress of blood or the like to the connector 9, 10, or 11 portion, almost no current flows, and the detected voltage between the terminals is substantially 0 V in every case, but when blood enters, current flows between the terminals, creating a difference in the detected voltage between these terminals. This is used to determine liquid ingress.

In the depicted determination table, either a "1" (error) or a "0" (no error) is shown for the sake of illustration, but as shown in the flowchart of FIG. 7, if any of |Va−Vb|, |Vb−Vc|, and |Va−Vc| is determined to be "1" (Yes), then at that point no subsequent determination need be performed. Also, the order in which |Va−Vb|, |Vb−Vc|, and |Va−Vc| are determined is not limited to what is depicted. Regardless of the order, error determination due to liquid ingress will be carried out if any one of |Va−Vb|, |Vb−Vc|, and |Va−Vc| is within the range of the specific threshold.

If it is determined that there is liquid ingress, the controller 23 produces and outputs information indicating the occurrence of an error due to liquid ingress, and displays this information (in this case, the information that a liquid ingress error has occurred) on the display component 24 (step S114 in FIG. 6). The information indicating that an error due to liquid ingress has occurred may be given, for example, in symbols such as error codes corresponding to details about the error that has occurred, or in text, an illustration, or the like.

The controller 23 then displays the error result and executes the specific error processing discussed above (step S115 in FIG. 6), and then performs end processing (steps S112 and S113 in FIG. 6).

In the above processing, the error determination processing may be performed on the basis of the ratios of Va/Vb, Vb/Vc, Va/Vc, or the like, instead of |Va−Vb|, |Vb−Vc|, and |Va−Vc|.

1-2-4 Measurement Processing

Figure 10:
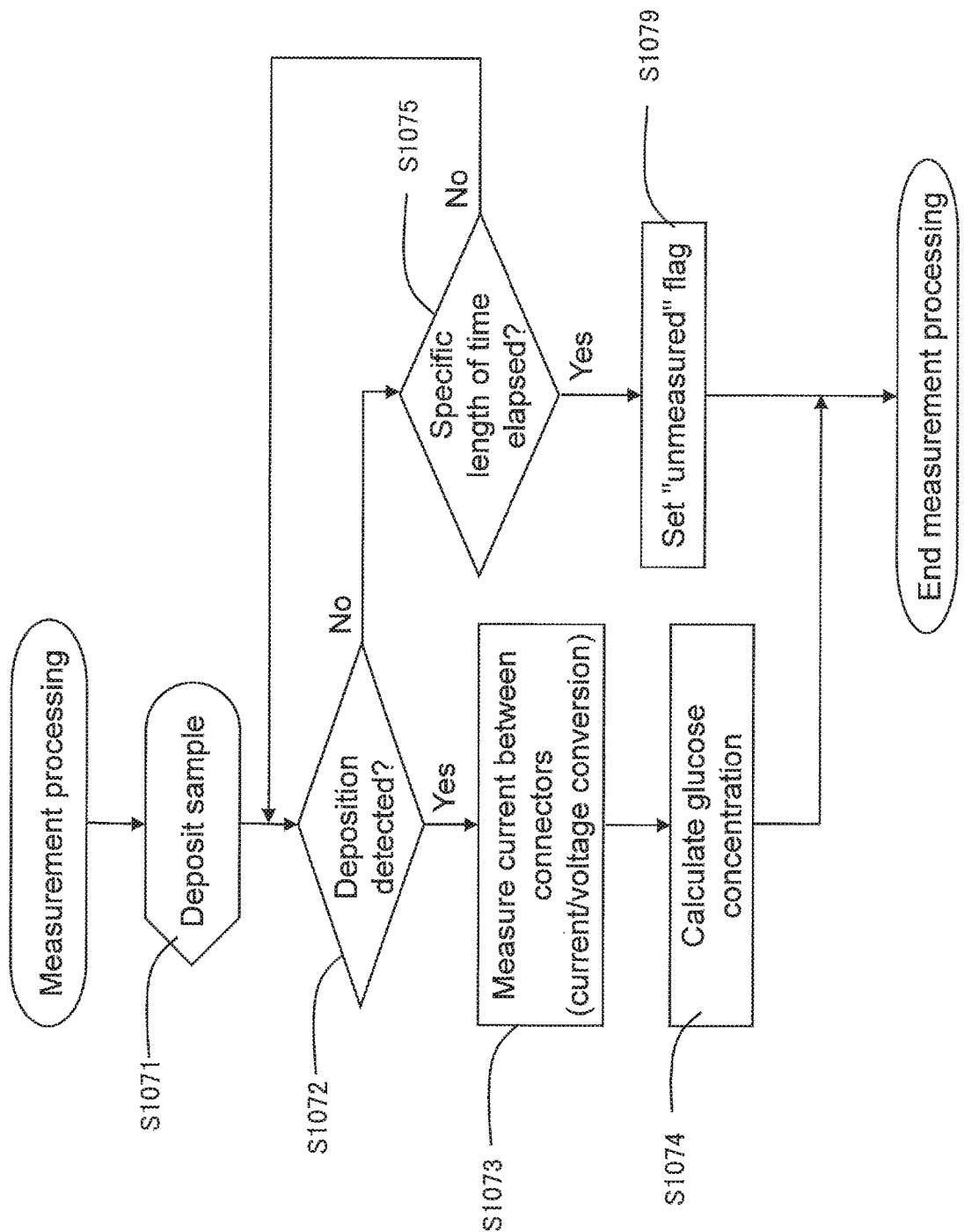
FIG. 10 is a flowchart of measurement processing performed by the biological information measurement device.

If it is determined in the above-mentioned liquid ingress determination processing (step S105) that there is no liquid ingress between the connectors 9, 10, and 11, then processing to measure a blood glucose level is performed after the start-up processing 2 (step S109 in FIG. 6). FIG. 10 shows the detailed flow in this measurement processing.

If no error is identified after the start-up processing 2 (step S108 in FIG. 6), the controller 23 enters a state in which it waits for blood to be deposited, and displays on the display component 24 a message prompting the user to deposit (instead of a message, this may be symbols, text, an illustration, or the like) (step S1071). At this point, the user uses the guide information displayed on the display component 24, voice information, or the like to deposit his own blood on the reagent side of the biosensor 2. The deposited blood goes through the biological sample supply port 16, and then to the blood component measurement counter electrode 6, the blood component measurement working electrode 5, and the blood component detecting electrode 7.

The controller 23 detects the deposition of blood (step S1072). When the deposition of blood is detected, the flow proceeds to step S1073.

When the deposition of blood is detected, the controller 23 measures the current between the connectors 9 and 10, between the connectors 10 and 11, and between the connectors 9 and 11, and acquires values obtained by converting these current values into voltage values (step S1073).

The controller 23 calculates the glucose concentration in the blood on the basis of the measured current, and outputs a measurement value (step S1074).

If the measurement is successful, the controller 23 outputs the blood glucose level as a measurement value and displays it on the display component 24 (step S111 in FIG. 6).

On the other hand, if the controller 23 does not detect the deposition of blood after a specific length of time has elapsed (step S1075), an "unmeasured" flag is set (step S1079), and the measurement processing is ended. After this the flow moves on to the main processing in FIG. 6, and the controller 23 causes the display component 24 to give a display indicating that measurement is ended (cancelled) (step S116 in FIG. 6), and performs the end processing (steps S112 and S113).

As described above, with the blood glucose level measurement device 100 pertaining to this embodiment, even in a state in which the biosensor 2 has been mounted, an error caused by the adhesion of a foreign substance, such as when blood flows into the connector 9, 10, or 11 portion, can be detected, and this prevents significant errors from occurring in the measurement results.

Also, since errors can be detected before blood is deposited on the biosensor 2, this avoids unnecessary puncture of the user's skin, and therefore reduces the burden on the user.

Also, since an error is outputted and displayed along with its cause, the user of the blood glucose level measurement device 100 can find out the cause of the error and take steps to ensure the proper measurement.

Embodiment 2

In Embodiment 1 above, an error caused by liquid ingress to the connector 9, 10, or 11 portion is identified on the basis of the difference or ratio of Va, Vb, and Vc obtained by converting the currents A, B, and C between the connectors 9, 10, and 11, but in this embodiment, the maximum and minimum values for Va, Vb, and Vc are used to identify an error caused by liquid ingress.

The error determination processing pertaining to this embodiment, which differs from that in Embodiment 1 above, will now be described. The rest of the configuration and functions are the same as those in Embodiment 1, so the same drawings and numbers will be used, and these will not be described again.

2-1 Error Determination Processing

Figure 11:
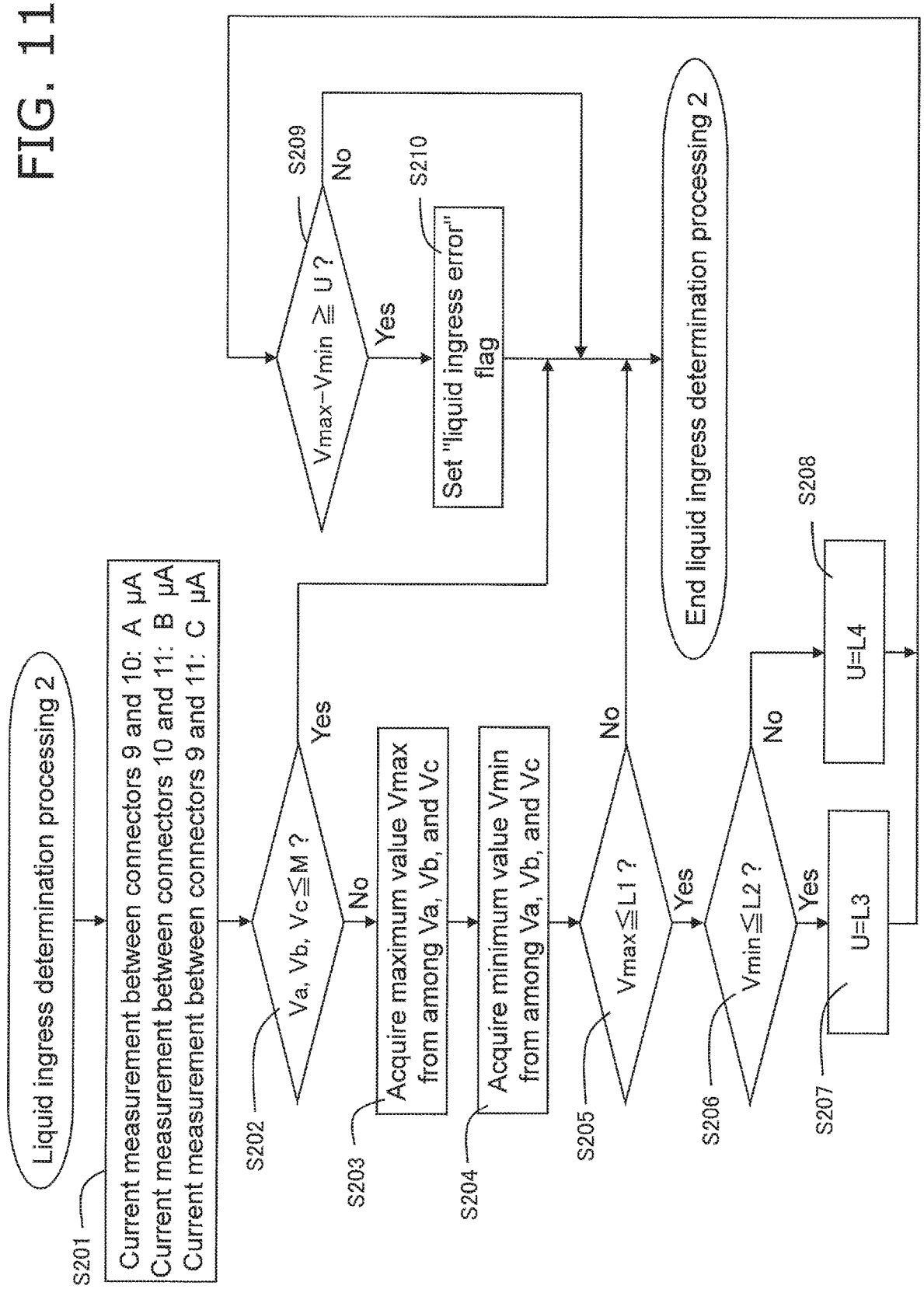
FIG. 11 is a flowchart of liquid ingress determination processing performed by a biological information measurement device pertaining to Embodiment 2.

FIG. 11 shows the error determination processing pertaining to this embodiment. This error determination processing is executed instead of the liquid ingress determination processing in FIG. 7, after the predetermined start-up processing 1 of S103 and S104 in FIG. 6. That is, Embodiment 2 involves a different liquid ingress determination processing.

The controller 23 supplies a specific voltage from the reference voltage source 19, through the switching circuit 18, between the connectors 9 and 10, between the connectors 10 and 11, and between the connectors 9 and 11. The current that flows between the connectors 9 and 10, between the connectors 10 and 11, and between the connectors 9 and 11 is converted into voltage by the current/voltage conversion circuit 21 and a numerical value by the A/D conversion circuit 22. The controller 23 measures this digitized voltage value as a detected voltage value.

More specifically, as shown in FIG. 8, the controller 23 acquires a current A ($\mu$A) between the connectors 9 and 10 (labeled as "between C9 and C10" in FIG. 8), a current B ($\mu$A) between the connectors 10 and 11 (labeled as "between C10 and C11" in FIG. 8), and a current C ($\mu$A) between the connectors 9 and 11 (labeled as "between C9 and C11" in FIG. 8) (step S201).

Next, the controller 23 determines whether or not voltage values Va, Vb, and Vc, obtained by converting current A, current B, and current C with the current/voltage conversion circuit 21 and the A/D conversion circuit 22, are equal to or less than a specific threshold M (an example of a second threshold) (step S202). M is a value corresponding to an amount of current used for confirming conductivity between terminals, and is set in a range of values corresponding to 0 to 3 $\mu$A. For example, if this is only used to confirm conductivity, it may be set to 0 $\mu$A (0 V), but if conductivity from something other than liquid ingress, such as absorption of reagent moisture, is excluded, it may be set to a value that exceeds 0 $\mu$A. If all of Va, Vb, and Vc do not exceed the specific threshold M, it is concluded that at least no liquid ingress has occurred, the error determination processing (liquid ingress determination processing 2) is ended, the flow moves on to the main processing in FIG. 6, proceeds to the start-up processing 2 of step S107, and then moves on to measurement processing (step S109 in the drawing).

If any of Va, Vb, and Vc exceeds the specific threshold M, the controller 23 acquires a value Vmax, which is the largest among Va, Vb, and Vc (step S203). The controller 23 also acquires a value Vmin, which is the smallest among Va, Vb, and Vc (step S204).

The controller 23 then determines whether or not Vmax is equal to or less than a specific threshold L1 (step S205). The threshold L1 is set in a range of values corresponding to 3 to 25 $\mu$A, for example. The controller 23 determines that there is no liquid ingress if Vmax exceeds the specific threshold L1, and just as above, this error determination processing is ended, the flow moves on to the main processing in FIG. 6, then proceeds to the start-up processing 2 of step S107, and then moves on to measurement processing (step S109 in the drawing). On the other hand, if Vmax is equal to or less than the specific threshold L1, the flow proceeds to step S206.

The controller 23 also determines whether or not Vmin is equal to or less than a specific threshold L2 (step S206). The threshold L2 is set in a range of values corresponding to 0.1 to 3 $\mu$A, for example. If Vmin is determined to exceed L2, the controller 23 sets a variable U to L3 (step S207), and if it is determined that Vmin is equal to or less than L2, the variable U is set to L4 (step S208). The thresholds L3 and L4 are each set in a range of values corresponding to 0.1 to 10 $\mu$A, for example, but so that L3<L4.

The controller 23 determines whether or not the difference between Vmax and Vmin is equal to or greater than the threshold U (an example of a first threshold) set in step S207 or S208 (step S209).

In step S209, the controller 23 sets a "liquid ingress error" flag if the difference between Vmax and Vmin is equal to or greater than he threshold U (step S210), and ends this error determination processing. After this, the flow moves on to the main processing in FIG. 6, and then moves on to the above-mentioned error display and error processing (steps S114 and S115 in FIG. 6). After this, the end processing is performed (steps S112 and S113).

On the other hand, if the difference between Vmax and Vmin is under the threshold U, the controller 23 determines that there is no liquid ingress, and just as above, this error determination processing is ended, the flow moves on to the main processing in FIG. 6, then proceeds to the start-up processing 2 in step S107, and moves on to the measurement processing (step S109 in the drawing).

FIG. 12 is a determination table produced by the liquid ingress determination processing pertaining to Embodiment 2. As shown in this table, if either of the conditions Vmax≤L1 and Vmax−Vmin≥U is not satisfied, it is determined that there is no ingress of blood or the like at the connector 9, 10, or 11 portion. Also, if the conditions Vmax≤L1 and Vmax−Vmin≥U are both satisfied, it is determined that there is a high probability that blood or the like has flowed into the connector 9, 10, or 11 portion.

In the depicted determination table, either a "1" (error) or a "0" (no error) is shown for the sake of illustration, but as shown in the flowchart of FIG. 11, if Vmax L1 is determined to be "0" (No), then at that point no subsequent determination need be performed. Also, the order of the determination processing is not limited to what is depicted, and may be changed.

Also, in the above processing, error determination processing may be performed on the basis of the ratios of Vmin/Vmax, etc., instead of Vmax−Vmin.

As described above, with the blood glucose level measurement device 100 pertaining to this embodiment, even in a state in which the biosensor 2 has been mounted, an error caused by the adhesion of a foreign substance, such as when blood flows into the connector 9, 10, or 11 portion, can be detected, and this prevents significant errors from occurring in the measurement results.

Also, since errors can be detected before blood is deposited on the biosensor 2, this avoids unnecessary puncture of the user's skin, and therefore reduces the burden on the user.

Also, since an error is outputted and displayed along with its cause, the user of the blood glucose level measurement device 100 can find out the cause of the error and take steps to ensure the proper measurement.

Embodiment 3

In this embodiment, just as in Embodiment 2, liquid ingress error determination is performed using the maximum and minimum values for Va, Vb, and Vc obtained by converting current A, current B, and current C between the connectors 9, 10, and 11, but this embodiment differs from Embodiment 2 in that a different threshold is used. The rest of the configuration and functions are the same as those in Embodiment 1, so the same drawings and numbers will be used, and these will not be described again.

3-1 Error Determination Processing

Figure 13:
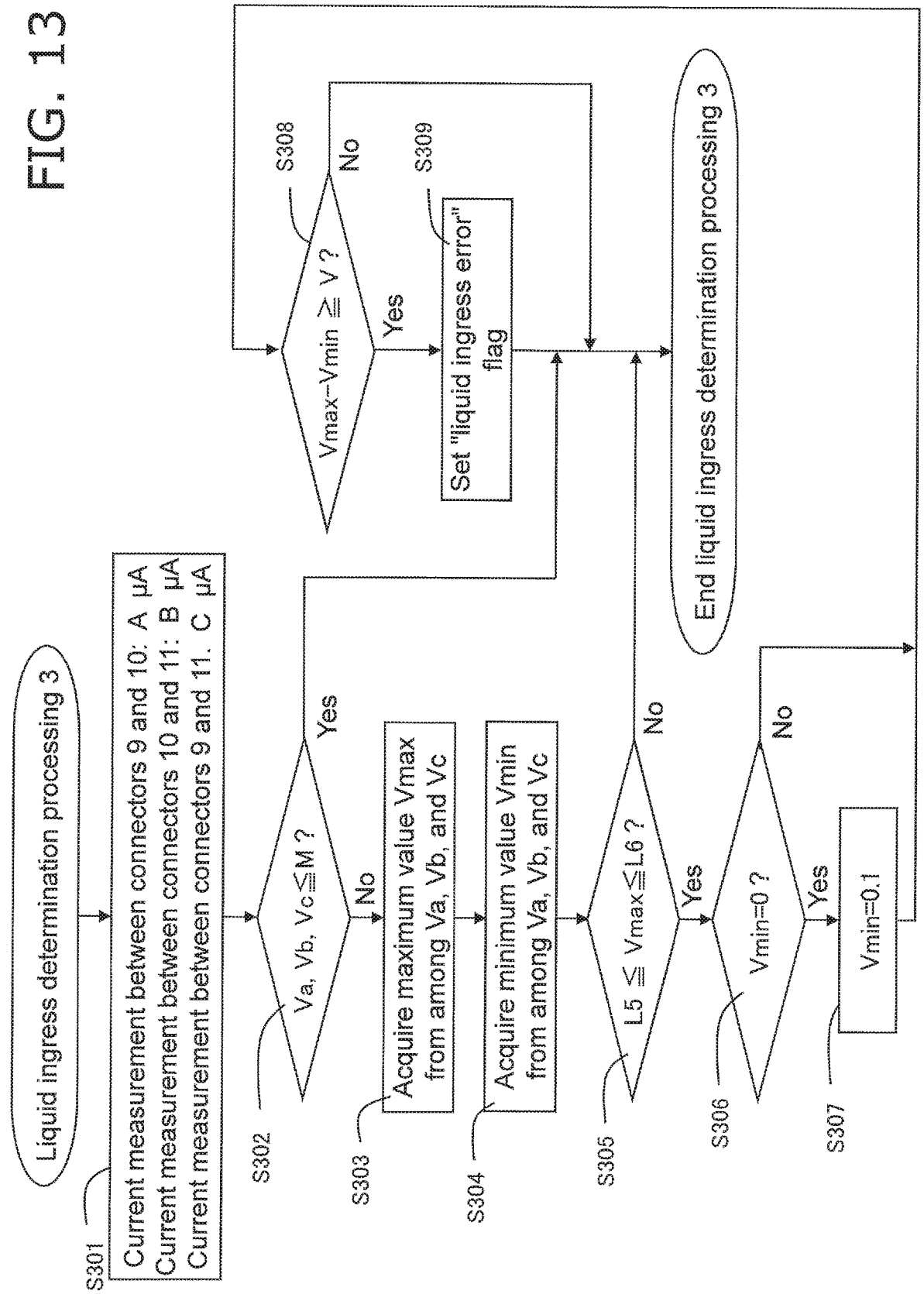
FIG. 13 is a flowchart of error determination processing performed by a biological information measurement device pertaining to Embodiment 3.

FIG. 13 shows the error determination processing pertaining to this embodiment. This error determination processing is executed instead of the liquid ingress determination processing in FIG. 7, after the start-up processing 1 of S103 in FIG. 6. That is, Embodiment 3 involves a different liquid ingress determination processing.

The controller 23 supplies a specific voltage from the reference voltage source 19, through the switching circuit 18, between the connectors 9 and 10, between the connectors 10 and 11, and between the connectors 9 and 11. The current that flows between the connectors 9 and 10, between the connectors 10 and 11, and between the connectors 9 and 11 is converted into voltage by the current/voltage conversion circuit 21 and a numerical value by the A/D conversion circuit 22. The controller 23 measures this digitized voltage value as a detected voltage value.

More specifically, as shown in FIG. 8, the controller 23 acquires a current A (µA) between the connectors 9 and 10 (labeled as "between C9 and C10" in FIG. 8), a current B (µA) between the connectors 10 and 11 (labeled as "between C10 and C11" in FIG. 8), and a current C (µA) between the connectors 9 and 11 (labeled as "between C9 and C11" in FIG. 8) (step S301).

Next, the controller 23 determines whether or not voltage values Va, Vb, and Vc, obtained by converting current A, current B, and current C with the current/voltage conversion circuit 21 and the A/D conversion circuit 22, are equal to or less than a specific threshold M (an example of a second threshold) (step S302). M is a value corresponding to an amount of current used for confirming conductivity between terminals, and is set in a range of values corresponding to 0 to 3 µA. For example, if this is only used to confirm conductivity, it may be set to 0 µA (0 V), but if conductivity from something other than liquid ingress, such as absorption of reagent moisture, is excluded, it may be set to a value that exceeds 0 µA. If all of Va, Vb, and Vc do not exceed the specific threshold M, it is concluded that at least no liquid ingress has occurred, the error determination processing (liquid ingress determination processing 3) is ended, the flow moves on to the main processing in FIG. 6, proceeds to the start-up processing 2 of step S107, and then moves on to measurement processing (step S109 in the drawing).

If any of Va, Vb, and Vc exceeds the specific threshold M, the controller 23 acquires a value Vmax, which is the largest among Va, Vb, and Vc (step S303). The controller 23 also acquires a value Vmin, which is the smallest among Va, Vb, and Vc (step S304).

The controller 23 then determines whether or not Vmax is within a range of from a specific threshold L5 to L6 (step S305). The threshold L5 is set in a range of values corresponding to 0 to 3 µA, for example. The threshold L6 is set in a range of values corresponding to 3 to 25 µA, for example. The controller 23 determines that there is no liquid ingress if Vmax is outside the range of from the specific threshold L5 to L6, this error determination processing is ended, the flow moves on to the main processing in FIG. 6, then proceeds to the start-up processing 2 of step S107, and then moves on to the measurement processing (step S109 in the drawing).

If Vmax is within the range of from the specific threshold L5 to L6, the controller 23 determines whether or not Vmin is zero (step S306).

If Vmin is zero, the controller 23 sets Vmin to 0.1 (step S307).

The controller 23 determines whether or not the difference between Vmax and Vmin is equal to or greater than a threshold V (an example of a first threshold) (step S308). The threshold V is set in a range of values corresponding to 0.1 to 10 µA. If the difference between Vmax and Vmin is equal to or greater than the threshold V, a "liquid ingress error" flag is set (step S309), and the error determination processing is ended. After this, the flow moves on to the main processing in FIG. 6, and moves on to the above-mentioned error display and error processing (steps S114 and S115 in FIG. 6). After this, the end processing is performed (steps S112 and S113).

On the other hand, if the difference between Vmax and Vmin is under the threshold V, the controller 23 determines that there is no liquid ingress, this error determination processing is ended, the flow moves on to the main processing in FIG. 6, then proceeds to the start-up processing 2 in step S107, and then moves on to the measurement processing (step S109 in the drawing).

FIG. 14 is a determination table produced by the liquid ingress determination processing pertaining to Embodiment 3. As shown in this table, if either of the conditions L5≤Vmax≤L6 and Vmax−Vmin≥V is not satisfied, it is determined that there is no ingress of blood or the like at the connector 9, 10, or 11 portion. On the other hand, if the conditions L5≤Vmax≤L6 and Vmax−Vmin≥V are both satisfied, it is determined that there is a high probability that blood or the like has flowed into the connector 9, 10, or 11 portion.

In the depicted determination table, either a "1" (error) or a "0" (no error) is shown for the sake of illustration, but as shown in the flowchart of FIG. 13, if L5≤Vmax≤L6 is determined to be "0" (No), then at that point no subsequent determination need be performed. Also, the order of the determination processing is not limited to what is depicted, and may be changed.

Also, in the above processing, error determination processing may be performed on the basis of the ratios of Vmin/Vmax, etc., instead of Vmax−Vmin.

As described above, with the blood glucose level measurement device 100 pertaining to this embodiment, even in a state in which the biosensor 2 has been mounted, an error caused by the adhesion of a foreign substance, such as when blood flows into the connector 9, 10, or 11 portion, can be detected, and this prevents significant errors from occurring in the measurement results.

Also, since errors can be detected before blood is deposited on the biosensor 2, this avoids unnecessary puncture of the user's skin, and therefore reduces the burden on the user.

Also, since an error is outputted and displayed along with its cause, the user of the blood glucose level measurement device 100 can find out the cause of the error and take steps to ensure the proper measurement.

Other Embodiments

Embodiments 1 and 2 were described above as illustrative of the technology disclosed herein, but the technology disclosed herein is not limited to or by these, and can also be applied to embodiments with modifications, substitutions, additions, omissions, and so forth made as needed.

Also, the various constituent elements described in Embodiments 1 and 2 can be combined to create new embodiments.

In view of this, some other examples of embodiments will now be given.

(1)

In the above embodiments, there were three connectors, but this is not the only option, and errors can be identified just as in the above embodiments when there are four or more connectors.

(2)

Error detection in the biological information measurement device pertaining to the above embodiments is not limited to the adhesion of blood or the like (a biological sample) between the connectors 9, 10, and 11. In addition, error detection is also possible for the adhesion of liquids and solids that are conductive (an example of the adhesion of a foreign sub stance).

(3)

In the above embodiments, the blood glucose level measurement device 100 is given as an example of a biological information measurement device, but this is not the only option, and the device may be any one that measures biological information (cholesterol level, neutral fat level, albumin level, globulin level, oxygen saturation, hemoglobin level, myoglobin level, uric acid level, etc.) by using a substance obtained from an organism (such as blood, urine, tissue, or cells) as a biological sample.

(4)

In the above embodiments, the start-up processing 1 (step S103 in FIG. 6) and the start-up processing 2 (step S107 in FIG. 6) are not limited to the order depicted in the drawings, and may be switched around.

(5)

The order in which the processing methods are executed in the above embodiments are not necessarily limited to that given in the above embodiments, and may be switched around without departing from the gist of the invention.

(6)

The present invention is not limited to being embodied as the biological information measurement device in the above embodiments, and can also be realized as a biosensor system that includes a biological information measurement device and a biosensor, or as an error detection method in a biological information measurement device.

INDUSTRIAL APPLICABILITY

The biological information measurement device disclosed herein is expected to find application as a biological information measurement device that detects blood glucose levels and other such biological information, for example.

The invention claimed is:

1. A method for error detection in a biological information measurement device comprising a controller, a sensor mounting component that mounts a sensor for measuring biological information on a basis of a biological sample, and a first connector, a second connector, and a third connector provided at the sensor mounting component, the error detection method comprising:

applying voltage between the first connector and the second connector, the second connector and the third connector, and the first connector and the third connector;

measuring a first current that flows between the first connector and the second connector, a second current that flows between the second connector and the third connector, and a third current that flows between the first connector and the third connector;

in a state in which the sensor is mounted to the sensor mounting component, determining that no foreign substance is adhered between any one of the first connector and the second connector, the second connector and the third connector, or the first connector and the third connector when all of a differential or a ratio between the first current and the second current, a differential or a ratio between the second current and the third current, and a differential or a ratio between the first current and the third current are outside a specific range and then, the controller enters a state in which it waits for the blood to be deposited for processing to measure when there is no foreign substance adhered, and the controller determines that there is the foreign substance adhered between the first connector and the second connector, the second connector and the third connector, or the first connector and the third connector when any of a differential or a ratio between the first current and the second current, a differential or a ratio between the second current and the third current, and a differential or a ratio between the first current and the third current is within the specific range of a specific threshold and, then outputs an error caused by the foreign substance adhered.

2. The method for error detection according to claim 1, wherein the controller determines no foreign substance adhered between at least two connectors included in the first connector, the second connector, and the third connector when the first current, the second current, and the third current are equal to or less than a specific threshold.

3. The method for error detection according to claim 1, the biological information measurement device further comprising a display component controlled by the controller, wherein the controller outputs the error caused by the foreign substance adhered to the display component when the controller determines that there is the foreign substance adhered between at least two connectors included in the first connector, the second connector, and the third connector, or when the controller determines that the sensor is a non-compatible sensor or a used sensor.

4. The method for error detection according to claim 1, the biological information measurement device further comprising a sensor detector that is connected to the controller and detects the mounting of the sensor to the sensor mounting component,
wherein the controller determines whether there is the foreign substance adhered between the first connector and the second connector, the second connector and the third connector, or the first connector and the third connector after the sensor detector has detected the mounting of the sensor to the sensor mounting component.

5. The method for error detection according to claim 1, wherein the controller determines whether the sensor is a non-compatible sensor or a used sensor after the controller has determined that there is no foreign substance adhered between any one of the first connector and the second connector, the second connector and the third connector, or the first connector and the third connector before the biological sample is deposited on the sensor.

* * * * *